United States Patent [19]

Merger et al.

[11] Patent Number: 4,497,963

[45] Date of Patent: Feb. 5, 1985

[54] PROCESS FOR THE PREPARATION OF AN ALIPHATIC, CYCLOALIPHATIC, AND/OR ALIPHATIC-CYCLOALIPHATIC DI- AND/OR POLYURETHANE

[75] Inventors: Franz Merger, Frankenthal; Friedrich Towae, Ludwigshafen, both of Fed. Rep. of Germany

[73] Assignee: BASF Aktiengesellschaft, Ludwigshafen, Fed. Rep. of Germany

[21] Appl. No.: 135,259

[22] Filed: Mar. 31, 1980

[30] Foreign Application Priority Data

Apr. 30, 1979 [DE] Fed. Rep. of Germany ....... 2917490

[51] Int. Cl.³ .......................................... C07C 125/073
[52] U.S. Cl. .................................... 560/115; 544/400; 560/158
[58] Field of Search ................. 560/24, 157, 115, 158; 544/400

[56] References Cited

U.S. PATENT DOCUMENTS 2,409,712  10/1946  Schweitzer ......................... 560/157
2,806,051  9/1957  Brockway ............................. 560/24
4,388,238  6/1983  Heitkamper ........................ 560/158

OTHER PUBLICATIONS

Morrison, "Organic Chemistry," 3rd Ed. pp. 318, 728, 729 (1974).

*Primary Examiner*—Michael L. Shippen
*Attorney, Agent, or Firm*—William G. Conger; Joseph D. Michaels

[57] ABSTRACT

A process for the preparation of an aliphatic, cyclo-aliphatic, and/or aliphatic-cycloaliphatic di- and/or polyurethane comprising the steps of A. reacting a primary aliphatic, cycloaliphatic, and/or aliphatic-cycloaliphatic di- and/or polyamine with a carbamate in the presence of alcohol at temperatures of 160° C. to 300° C., and B. separating the ammonia and other by-products from the aliphatic, cycloaliphatic, and/or aliphatic-cycloaliphatic di- and/or polyurethane.

One or more catalysts may be added to the reactants to increase the reaction rate. The aliphatic, cycloaliphatic, and/or aliphatic-cycloaliphatic di- and/or polyurethanes produced are valuable end and intermediate products. They can be transferred into the corresponding isocyanates which can then be used for the preparation of polyurethanes.

11 Claims, No Drawings

PROCESS FOR THE PREPARATION OF AN ALIPHATIC, CYCLOALIPHATIC, AND/OR ALIPHATIC-CYCLOALIPHATIC DI- AND/OR POLYURETHANE

BACKGROUND OF THE INVENTION

1. Field of the Invention

The invention pertains to the preparation of an aliphatic, cycloaliphatic, and/or aliphatic-cycloaliphatic di-and/or polyurethane by reacting a primary aliphatic, cycloaliphatic, and/or aliphatic-cycloaliphatic di- and-/or polyamine, with an O-alkyl carbamate in the presence of an alcohol.

2. Description of the Prior Art

On an industrial scale, N-substituted urethanes are normally produced by the reaction of alcohols with isocyanates or by the reaction of amines with chlorocarbonates. The isocyanates and chlorocarbonates used in these reactions are obtained by phosgenation of the corresponding amines or the corresponding alcohols. Houben-Weyl, *Methods of Organic Chemistry*, Vol. 8, pages 137, 120 and 101, (Georg Thieme Publishers, Stuttgart, 1952). These processes are very expensive and phosgene must be used with care because of its potential danger to man and the environment.

N-substituted urethanes are used as intermediates and end products. For instance, German Published Application No. 26 35 490 and U.S. Pat. No. 3,919,278 disclose the use of N-substituted urethanes for the manufacture of isocyanates. Because of their utility, many attempts have been made to develop better methods for preparing N-substituted urethanes. These methods and their shortcomings will be discussed.

German Published Application No. 21 60 111 describes a process for the manufacture of N-substituted urethanes by reacting an organic carbonate with a primary or secondary amine in the presence of a Lewis acid. There are several problems with this process. The conversion rates are rather low and the reaction times are long. Furthermore, N-alkylarylamines are always produced as by-products.

U.S. Pat. No. 2,834,799 describes a process for making carbamic and carbonic esters by the reaction of urea with alcohols in the presence of boron trifluoride. The problem with this method is that the boron trifluoride is required in equimolar quantities so that at least one molecule of boron trifluoride is used per molecule of produced carbamic ester and at least two molecules of boron trifluoride are consumed per molecule of carbonic ester. This process is not only expensive, but it causes problems in the environment because the boron trifluoride is produced in the form of the $H_3N \cdot BF_3$ adduct.

R. A. Franz et al, *Journal of Organic Chemistry*, Vol. 28, page 585 (1963) describe a process for making methyl-N-phenyl urethane from carbon monoxide, sulfur, aniline, and methanol. Very low yields are produced by this method; the yield does not exceed 25 percent even when there is a long reaction period.

U.S. Pat. No. 2,409,712 describes a process for making N-alkyl and N-aryl urethanes by the reaction of monoamines with urea (either N,N'-dialkyl- or N,N'-diarylurea is used) and alcohols at temperatures of 150° C. to 350° C. under increased pressure. It should be noted that this patent only describes the manufacture of N-alkylmonourethanes and does not mention the manufacture of N,N'-disubstituted diurethanes and polyurethanes. U.S. Pat. No. 2,677,698 also describes a process for the manufacture of N-substituted monourethanes. In this process, the urea is initially converted into the corresponding N,N'-disubstituted urea with monoamines, is then cleaned, and subsequently is reacted with an alcohol. The processes described are expensive and the yields are very low. Attempts to improve the yield by improving the methods of preparing and purifying the N,N'-disubstituted ureas have been unsuccessful.

Other processes have not been successful in eliminating the problems described thus far. U.S. Pat. No. 2,806,051 describes a process whereby N-substituted urethanes are produced by reacting n-hexylamine with urea and alcohol at a mole ratio of 1.0:1.2:2.0 at temperatures below 200° C., preferably of 120° C. to 160° C. Even in the preferably used temperature range, this process produces only small yields of N-substituted urethanes if the reaction time is limited to a period which is practical in an industrial setting. In view of the problems with this process, it is not surprising that U.S. Pat. No. 3,076,007, which describes the manufacture of N-alkyl- and N-cycloalkyl urethanes, does not incorporate the abovereferenced methods in its process. It does, however, describe the reaction of phosgene with alcohols to form chloroalkylformates, and it describes their subsequent reaction with amines to form urethanes. It also discloses the reaction of amines with ethylene carbonate to form urethanes.

None of the references cited discloses the preparation of aliphatic and cycloaliphatic di- and/or polyurethane by reacting a diamine with an O-alkyl carbamate in the presence of alcohol at temperatures of 160° C. to 300° C. It is surprising that aliphatic and cycloaliphatic di- and/or polyurethane can be produced in one process stage with good yields by reacting an O-alkyl carbamate with a diamine in the presence of alcohol at temperatures of 160° C. to 300° C. It is known that ethyl carbamates in boiling dioxane do not react with amines [D.G. Crosby and C. Niemann, *Journal of the American Chemical Society*, Vol. 76, page 4458 (1954)], and that the reaction of N-alkyl urethanes with alcoholic ammonia solution at temperatures of 160° C. to 180° C. results in an alkaline solution from which amine hydrochloride, urea, alkyl urea, and alkyl urethane can be isolated after neutralization with hydrochloric acid [M. Brander, *Rec. trav. chim.*, Vol. 37, pages 88–91 (1917)]. Moreover, the manufacture of N-monosubstituted carbamates from monoamines, urea and alochols, and/or the exchange of the amino group in the carbamates succeeds with small yields only.

Prior teachings also indicate that corresponding di-ureas are obtained from diamines and O-alkyl carbamates; for example, hexamethylenediurea is obtained from hexamethylenediamine and carbamates. It is also known that, although urea and alcohol may react to produce urethanes, they continue to react to form N,N'-di-substituted ureas in the presence of amines. See Houben-Weyl, *Methods of Organic Chemistry*, Vol. 8, pages 151 and 140, (Georg Thieme Publishers, Stuttgart, 1952). These side reactions decrease the yield of the desired product.

Furthermore, German Pat. No. 896 412 indicates that high molecular, spinnable condensation products may be produced from the diamides of carbonic acid such as urea and diamines. This result is likely to occur if the amino groups of the diamines are separated by a chain of more than three atoms. U.S. Pat. No. 2,181,663 and U.S. Pat. No. 2,568,885, for instance, disclose that high molecular polyureas with molecular weights of 8000 to 10,000 and greater, may be produced when diurethanes are condensed with diamines at temperatures of approximately 150° C. to 300° C. Moreover, mono- and polyurethanes can be split thermally into isocyanates, alcohols and possibly olefins, carbon dioxide, urea and carbodiimide, and these products can be split into products such as biurets, allophanates, isocyanurates, polycarbodiimides, and others. See *The Journal of the American Chemical Society,* Vol. 80, page 5495 (1958) and Vol. 48, page 1946 (1956).

In view of the problems identified in the prior art, it was surprising that our process, which involved very similar reaction conditions, would result in di- and/or polyurethane with very good yields. It was particularly surprising because when diurethanes were prepared from the products mentioned in the previous paragraph acccording to the reaction conditions of our invention, good yields did not result.

SUMMARY OF THE INVENTION

The purpose of this invention was to produce an aliphatic, cycloaliphatic, and/or aliphatic-cycloaliphatic di- and/or polyurethane from readily available raw materials in one reaction stage under economically justifiable conditions with good yields. The use of strongly toxic raw materials such as phosgene, carbon monoxide, or catalysts which are toxic and form toxic compounds during the reaction, such as hydrogen sulfide, was to be avoided.

The problem was solved by developing a process for the preparation of an aliphatic, cycloaliphatic, and/or aliphatic-cycloaliphatic di- and/or polyurethane comprising the steps of A. reacting a primary aliphatic, cycloaliphatic, and/or aliphatic-cycloaliphatic di- and/or polyamine with an O-alkyl carbamate in the presence of an alcohol at temperatures of 160° C, to 300° C., and B. separating the ammonia and other by-products from the aliphatic and/or cycloaliphatic di- and/or polyurethane.

One or more catalysts may be added to the reactants in order to increase the reaction rate.

The reaction may be illustrated by the following equation:

$$R-(NH_2)_n + n\, H_2NCOOR' \xrightarrow{R'OH} R-(NHCOOR')_n + nNH_3$$

The aliphatic and/or cycloaliphatic di- and/or polyurethanes produced according to the process of this invention are valuable end and intermediate products. They are used, for instance, as pesticides. As intermediate products, they are used as components for polycondensation and polymer systems and, in particular, they are transferred into the corresponding di- and/or polyisocyanates by removal of the alcohol. The di- and/or polyisocyanates can be used in the manufacture of polyurethanes.

DESCRIPTION OF THE PREFERRED EMBODIMENTS

In order to prepare the aliphatic and/or cycloaliphatic di- and/or polyurethanes in accordance with the process of this invention, a primary aliphatic, cycloaliphatic, and/or aliphatic-cycloaliphatic di- and/or polyamine is reacted with an O-alkyl carbamate in the presence of an alcohol in such quantities that the ratio of amino groups of the amines to the O-alkyl carbamate is 1:0.8 to 10, preferably 1:0.9 to 2.5 and in particular, 1:1 to 2.

The reaction preferably is carried out in the presence of excess alcohol at temperatures of 160° C. to 300° C. at normal pressure or under reduced or increased pressure. One or more catalysts may be added to the reaction mixture in order to increase the reaction rate. It has proven to be advantageous to immediately remove the resultant ammonia from the reaction mixture, for instance, by means of distillation.

Amines having the formula $R-(NH_2)_n$ are well suited for the reaction with the O-alkyl carbamate in the presence in alcohol according to this invention. In the formula, R represents a multifunctional possibly substituted aliphatic or cycloaliphatic radical or mixed radicals of this type; and n stands for a whole number, the value of which corresponds with the valency of R and is at least 2, and preferably 2 to 5, and particularly 2. The aliphatic radicals contain 2 to 20, preferably 4 to 16, and particularly 4 to 12, carbon atoms; they may have a straight chain or a branched structure; and they may contain interspersed heteroatoms such as oxygen, sulfur or a tertiary nitrogen atom, or bivalent hererocyclic radicals as bridge members in bonded form. The cycloalphatic radicals contain 5 to 12, preferably 6 to 12, carbon atoms whereas the mixed radicals of this type show 8 to 50, preferably 10 to 15, carbon atoms. Examples to be mentioned in detail include: aliphatic diamines such as ethylene diamine, 1,3 and 1,2-propanediamine, 2,2-dimethyl-1,3-propanediamine, 1,4-butanediamine, 1,5-pentamethylenediamine, 1,6- hexamethylenediamine, 2,2,4-trimethyl-1,6-hexamethylenediamine, 1,8-octamethylenediamine, 1,10-decylenediamine, and 1,12-dodecylenediamine; cycloaliphatic diamines such as 1,2- 1,3- and 1,4-cyclohexanediamine, 2,4- and 2,6-hexahydrotoluenediamine, as well as the corresponding isomer mixture; aliphatic-cycloaliphatic diamines such as 1,4-hexahydroxylenediamine, 4,4'- 2, 4'- and 2,2'-diaminodicyclohexylmethane as well as the corresponding isomer mixtures, 2,2-bis(4-aminocyclohexyl)propane, 3-aminomethyl-3,5,5-trimethylcyclohexylamine; dicyclopentadienyl compounds having the formula

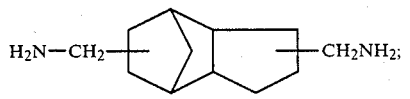

polyamines such as polycyclohexyl polymethylene polyamines having the formula

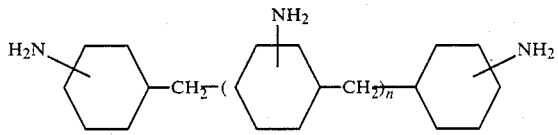

wherein n=1 to 4; and diamines containing, in bonded form, mixtures of diaminodicyclohexylmethanes and polycyclohexyl polymethylene polyamines and heteroatoms or heterocyclic radicals such as 3,3'-diaminodipropyl ether, possibly substituted N,N'-bis(aminoalkyl)-piperazine, for instance, N,N'bis-(2,2-dimethyl -3- aminopropyl) piperazine and N,N'-bis(aminopropyl)-piperazine.

Preferably used as amines are 1,6-hexamethylene diamine, 2,2,4-trimethyl-1,6-hexamethylenediamine, 1,4-hexahydroxylenediamine, 2,4- and 2,6-hexahydrotoluenediamine as well as the corresponding isomer mixtures, 4,4'-diaminodicyclohexylmethane, 1,4-diaminocyclohexane, 2,2-bis(4-aminocyclohexyl)-propane and 3-aminomethyl-3,5,5-trimethylcyclohexylamines.

Suitable O-alkyl carbamates for the reaction have the formula $H_2N-COOR'$ in which R' represents a possibly substituted aliphatic, cycloaliphatic or aromatic-aliphatic radical. O-alkyl carbamates based on primary aliphatic monoalcohols having 1 to 20 carbon atoms, preferably 1 to 10 carbon atoms, such as methyl carbamate, ethyl carbamate, propyl carbamate, N-butyl carbamate, isobutyl carbamate, -2- and -3-methylbutyl carbamate, neopentyl carbamate, 2-ethylbutyl carbamate, 2-methylpentyl carbamate, n-hexyl carbamate, 2-ethylhexyl carbamate, heptyl carbamate, n-octyl carbamate, n-nonyl carbamate, n-decyl carbamate, n-dodecyl carbamate, 2-phenylpropyl carbamate, and carbamates based on secondary aliphatic and cycloaliphatic monoalcohols having 3 to 15 carbon atoms, preferably 3 to 6 carbon atoms, such as isopropyl carbamate, sec-butyl carbamate, sec-isoamyl carbamate, cyclopentyl carbamate, cyclohexyl carbamate, methylcyclohexyl carbamate, and tertiary butylcyclohexyl carbamate may be used. Preferably used, however, are methyl carbamate, ethyl carbamate, propyl carbamate, butyl carbamate, isobutyl carbamate, 2-ethylbutyl carbamate, 2- and 3-methylbutyl carbamate, 2-methylpentyl carbamate, 2-ethylhexyl carbamate, heptyl carbamate, octyl carbamate and cyclohexyl carbamate.

Any desired alcohol unsubstituted or substituted primary or secondary aliphatic alcohol, as well as mixtures thereof, can be used as alcohols for the process according to this invention. Preferably used is the alcohol corresponding to the carbamate in such quantities that the ratio of amino groups of the aliphatic and/or cycloaliphatic amines to hydroxyl groups of the alcohols is 1:0.25 to 50, preferably 1:0.5 to 15 and particularly, 1:0.5 to 7.5.

Examples include primary aliphatic monoalcohols having 1 to 20 carbon atoms, preferably 1 to 10 carbon atoms, such as methanol, ethanol, propanol, n-butanol, 2-ethylbutanol, neopentyl glycol, pentanol, 2-methylpentanol, n-hexanol, 2-ethylhexanol, n-heptanol, n-octanol, n-decanol, n-dodecanol, 2-phenylpropanol and benzyl alcohol; and secondary aliphatic and cycloaliphatic monoalcohols having 3 to 15 carbon atoms, preferably 3 to 6 carbon atoms, such as isopropanol, sec-butanol, sec-isoamyl alcohol, cyclopentanol, cyclohexanol, methylcyclohexanol, and 4-tertiarybutylcyclohexanol. Preferably used are the monoalcohols, methanol, ethanol, propanol, n-butanol, isobutanol, 2- and 3-methylbutanol, 2-ethylbutanol, n-pentanol, 2-methylpentanol, n-hexanol, 2-ethylhexanol, heptanol, octanol, and cyclohexanol.

If so required, the alcohols may also be mixed with other organic solvents which are inert under reaction conditions. Alcohol-solvent mixtures containing at least 20 percent by weight, preferably more than 50 percent by weight, of alcohol relative to the total weight can be used.

According to this invention, the aliphatic and/or cycloaliphatic di- and/or polyurethanes, preferably the diurethanes, are appropriately produced in the absence of catalysts since the reaction normally takes place in economically acceptable reaction times and with good yields. This avoids costly cleaning operations for removing the catalysts from the resultant end products.

If catalysts are used in order to increase the rate of reaction, preferably at low temperatures, they should be used in quantities of 0.1 to 20 percent by weight, preferably 0.5 to 10 percent by weight, and in particular 1 to 5 percent by weight relative to the weight of the primary di- or polyamine. Suitable catalysts are inorganic or organic compounds containing one or more, preferably one, cation of metals of the groups IA, IB, IIA, IIB, IIIA, IIIB, IVA, IVB, VA, VB, VIB, VIIB and VIIIB of the periodic systems defined in accordance with the *Handbook of Chemistry and Physics*, (14th edition, Chemical Rubber Publishing Company, 2310 Superior Avenue N.W., Cleveland, Ohio). These compounds include, for instance, halides such as chlorides and bromides, sulfates, phosphates, nitrates, borates, hydroxides, carboxylates, chelates, carbonates, and thio- or dithiocarbamates. The compounds should contain cations of any of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Preferably used are the cations of lithium, calcium, aluminum, tin, bismuth, antimony, copper, zinc, titanium, vanadium, chromium, molybdenum, manganese, iron and cobalt. Without any recognizable marked drawbacks, the catalysts may also be used in the form of their hydrates or ammoniates.

Examples of typical catalysts include the following compounds: lithium methanolate, lithium ethanolate, lithium propanolate, lithium butanolate, sodium methanolate, potassium-tertiary butanolate, magnesium methanolate, calcium methanolate, tin-(II)-chloride, tin-(IV)-chloride, lead acetate, lead phosphate, antimony-(III)-chloride, antimony(V)-chloride, aluminum isobutylate, aluminum trichloride, bismuth-(III)-chloride, copper-(II)-acetate, copper-(II)-sulfate, copper-(II)-nitrate, bis-(triphenylphosphineoxido)-copper-(II)-chloride, copper molybdate, silver acetate, gold acetate, zinc oxide, zinc chloride, zinc acetate, zinc acetonyl acetate, zinc octoate, zinc oxylate, zinc hexylate, zinc benzoate, zinc undecylenate, cerium-(IV)-oxide, uranyl acetate, titanium tetrabutanylate, titanium tetrachloride, titanium tetraphenolate, titanium naphthenate, vanadium-(III)-chloride, vanadium acetonylacetate, chromium-(III)-chloride, molybdenum-(VI)-oxide, molybdenum acetylacetonate, tungsten-(VI)-oxide, manganese-(II)-chloride, manganese-(II)-acetate, manganese-(III)-acetate, iron-(II)-acetate, iron-(III)-acetate, iron phosphate, iron oxylate, iron-(III)-chloride, iron-(III)-bromide, cobalt acetate, cobalt chloride, cobalt sulfate, cobalt naphthenate, nickel chloride, nickel acetate and nickel naphthenate as well as their mixtures.

The reaction takes place at temperatures of 160° C. to 300° C., preferably of 180° C. to 250° C., and particularly from 185° C. to 230° C.; and at pressures of 0.1 bar to 120 bars, preferably 0.5 bar to 60 bars, and in particular from 1 bar to 40 bars. The reaction times which are appropriate for the corresponding temperature ranges are 0.1 hour to 50 hours, preferably 3 hours to 20 hours, and particularly 5 hours to 15 hours. With a given temperature, the reaction is then preferably carried out under a pressure which allows the resultant ammonia to be selectively distilled out of the reaction mixture. The corresponding values may be taken from tables of physical characteristic data for ammonia and alcohols.

One effective way of preparing the di- and/or polyurethanes is to mix the reactants in the corresponding mole ratios, in the presence or absence of catalysts, in a pressurized or unpressurized reaction vessel equipped with a device for separating the ammonia, and then heat the mixture. The resulting ammonia can be separated after the reaction has been completed. Preferably, however, it is distilled off during the reaction. It may be advantageous, particularly in the case of the reaction of low molecular alcohols under pressure, to separate the ammonia by using a stripping agent which is inert under the reaction conditions, such as a gas like nitrogen.

A particularly advantageous method of preparing the di- and/or polyurethanes which, as a rule, results in a considerable reduction of the reaction time, is described as follows: (1) The primary aliphatic and/or cycloaliphatic di- and/or polyamines, the urea, and the alcohol are initially reacted in a ratio of the amino groups of the amines to O-alkyl carbamate to hydroxyl groups of the alcohol of 1:1–1.5:0:1–1, preferably 1:1–1.25:0.25–0.75 for 1 hour to 4 hours, preferably 2 hours to 3 hours. (2) Subsequently, additional alcohol is added to the reaction mixture in an amount such that 1.5 to 7.5, preferably 2 to 5 moles of alcohol are present per $NH_2$ group of the amine and such that the reaction is completed in a total time period of 4 hours to 20 hours, preferably 5 hours to 15 hours. (3) Thereafter, before or after removing the catalyst and/or filtering out solid materials, the di- and/or polyurethanes are isolated from the resulting reaction mixture. This may be done, for instance, by completely distilling off the alcohol and/or the solvent as well as any O-alkyl carbamates which are formed as by-products, by partially distilling off the alcohol and crystallization, by crystallization, or by precipitation with or transcrystallization from other solvents.

The parts referred to in the specific examples which follow are relative to weight. The elementary compositions and structures were confirmed by elementary analysis, mass spectrometry, as well as infra-red and nuclear magnetic resonance spectra.

EXAMPLE 1

Agitated in a reaction vessel are 116 parts of 1,6-hexamethylenediamine with 346 parts of O-octyl carbamate and 2000 parts of n-octanol-(1) at a reflux temperature of 185° C.–195° C. for 16 hours while the ammonia is removed by distillation. The precipitate formed in the reaction mixture, cooled to 100° C.–110° C., is removed by filtration. The reaction product is allowed to crystallize by cooling to room temperature. By means of filtration, washing with n-octanol-(1) and drying, 236 parts of 1,6-bis(octoxycarbonylamino)hexane, $C_{24}H_{48}N_2O_4$ (molecular weight 428), are obtained corresponding with 55 percent of theory relative to 1,6-hexamethylenediamine and O-octylcarbamate. The melting point is 106° C.–108° C. (from ethyl acetate).

EXMAPLE 2

Agitated in a reaction vessel are 116 parts of 1,6-hexamethylenediamine with 346 parts of O-octyl carbamate, 3 parts sodium octylate and 1500 parts of n-octanol at a reflux temperature of 185° C.–195° C. for 12 hours while the ammonia is removed by distillation. The resulting precipitate is removed from the reaction mixture by means of filtration after cooling to 100° C.–110° C. The reaction is allowed to crystallize by cooling to room temperature. By means of filtration, washing with n-octanol and drying, 242 parts of 1,6-bis-(octoxycarbonylamino)hexane is obtained corresponding with 56.5 percent of theory. The melting point is 106° C.–107° C.

EXAMPLE 3

Agitated in a reaction vessel are 116 parts of 1,6-hexamethylenediamine with 380 parts of O-octyl carbamate and 130 parts of n-octanol-(1) at a reflux temperature of 185° C.–205° C. for 2 hours while the ammonia is removed by distillation. At this point, an additional 500 parts of n-octanol-(1) are allowed to flow into the reaction mixture and the reaction is continued at reflux temperature for 7 hours. The reaction mixture, cooled to 110° C., is filtered, and the reaction product is allowed to crystallize by cooling. By filtration, washing with n-octanol-(1) and drying, 388 parts of 1,6-bis(octoxycarbonylamino)hexane are obtained corresponding with 90.6 percent theory relative to 1,6-hexamethylenediamine. The melting point is 107° C.–109° C.

EXAMPLE 4

Agitated in a reaction vessel are 232 parts of 1,6-hexamethylenediamine with 550 parts of O-butyl carbamate and 200 parts of n-butanol at a reflux temperature of 185° C.–195° C. and 6 bars to 7 bars accompanied by a throughput of 10 liters of nitrogen per liter of reaction mixture an hour via a dip tube for a period of 3 hours. At this point, an additional 500 parts of n-butanol are allowed to flow into the reaction mixture and the reaction is continued at 195° C.–200° C. and approximately 7 bars for 8 hours. By cooling the reaction mixture, the product is allowed to crystallize. By filtration and transcrystallization from acetone/water, 563 parts of 1,6-bis(butoxycarbonylamino)hexane, $C_{16}H_{32}N_2O_4$ (molecular weight 316) are obtained corresponding with 89 percent of theory relative to 1,6-hexamethylenediamine. The melting point is 90° C.–91° C.

EXAMPLE 5

Agitated in a reaction vessel are 232 parts of 1,6-hexamethylenediamine with 800 parts of O-ethyl carbamate and 120 parts ethanol at a reflux temperature of 185° C.–195° C. and 23 bars to 25 bars for two hours. At this point, an additional 500 parts of ethanol are allowed to flow into the reaction mixture and the reaction is continued at 195° C.–200° C. for 8 hours accompanied by the throughput of 8 liters of nitrogen per liter of reaction mixture an hour. The reaction mixture is largely concentrated by removing ethanol via distillation and the product is transcrystallized from acetone/water. Obtained are 432 parts of bis(ethoxycarbonylamino)-hexane, $C_{12}H_{24}N_2O_4$ (molecular weight 260) corresponding with 83 percent of theory relative to 1,6-hexamethylenediamine. The melting point is 80° C.–82° C.

EXAMPLE 6

Agitated in a reaction vessel are 116 parts of 1,6-hexamethylenediamine with 300 parts of O-cyclohexyl carbamate and 140 parts of cyclohexanol at a reflux temperature of 185° C.–195° C. and, a pressure of 2 bars to 3 bars for two hours. At that point, an additional 600 parts of cyclohexanol are allowed to flow into the reaction mixture and the reaction is continued at 195° C.–200° C. for 8 hours accompanied by a throughput of 10 liters of nitrogen per hour per liter of reaction mixture. The reaction mixture is allowed to cool to approximately 100° C. and the filtrate is concentrated by means of distillation to a sump temperature of approximately 180° C. at 5 millibars to 10 millibars. By crystallizing the residue from methanol/water, 287 parts of 1,6-bis(cyclohexoxycarbonylamino)hexane, $C_{20}H_{36}N_2O_4$ (molecular weight 368) are obtained corresponding with 78 percent of theory. The melting point is 98° C.–100° C.

EXAMPLE 7

Agitated in a reaction vessel 116 parts of 1,6-hexamethylenediamine with 360 parts of 2-butoxyethoxy carbamate and 118 parts of 2-butoxyethanol-(1) at a reflux temperature of 180° C.–200° C. for two hours while the ammonia is removed by means of distillation. At this point, an additional 750 parts of 2-butoxyethanol-(1) are allowed to flow into the reaction mixture and the reaction is continued at reflux temperature for 7 hours. The unreacted 2-butoxyethanol is largely removed by distillation in a water-jet vacuum, and the residue is crystalized from methanol/water. By filtration and drying, 355 parts of 1,6-bis(2-butoxyethoxycarbonylamino)hexane, $C_{20}H_{40}N_2O_6$ (molecular weight 404), are obtained corresponding with 87.8 percent of theory relative to 1,6-hexamethylenediamine. The melting point is 64° C.–65° C.

EXAMPLE 8

Agitated in a reaction vessel are 142 parts of 1,4-hexahydroxylenediamine with 380 parts of O-octyl carbamate and 150 parts of n-octanol-(1) at a reflux temperature of 185° C.–200° C. for 2 hours while the ammonia is removed by means of distillation. At that point, an additional 600 parts of n-octanol are allowed to flow into the reaction mixture and the reaction is continued at reflux temperature for 8 hours. The reaction mixture, cooled to 110° C., is filtered, and the product is allowed to crystallize by cooling to room temperature. By filtration, washing with octanol-(1) and drying, 411 parts of 1,4-bis(octoxycarbonylaminomethyl)cyclohexane, $C_{26}H_{50}N_2O_4$ (molecular weight 454) are obtained corresponding with 90.5 percent theory relative to 1,4-hexahydroxylenediamine. The melting point is 120° C.–122° C. (from ethyl acetate).

EXAMPLE 9

Agitated in a reaction vessel are 210 parts of 4,4'-diaminodicyclohexylmethane with 360 parts of O-octyl carbamate and 150 parts of n-octanol-(1) at a reflux temperature of 185° C.–205° C. for 2 hours while the ammonia is removed by means of distillation. At this point, an additional 650 parts of n-octanol are allowed to flow into the reaction mixture and the reaction is continued at reflux temperature for 10 hours. The reaction mixture, which has been cooled to 100° C., is filtered, and the product is allowed to crystallize by cooling the filtrate. By filtration, washing with octanol and drying, 468 parts of bis(4-octoxycarbonylaminocyclohexyl)methane, $C_{31}H_{58}N_2O_4$ (molecular weight 522) are obtained corresponding with 89.6 percent theory relative to 4,4'-bisaminodicyclohexylmethane. The melting point is 129° C.–130° C.

EXAMPLE 10

Agitated in a reaction vessel are 156 parts of bis(3-aminopropyl) ether with 520 parts of O-octyl carbamate and 1000 parts of n-octanol-(1) at a reflux temperature of 185° C.–200° C. for 15 hours while the ammonia is removed by means of distillation. Unreacted octanol and O-octylcarbamate are quickly removed by filtration and distillation up to a sump temperature of 180° C.–200° C. at approximately 2 millibars. Upon cooling, one obtains a crystallizing residue of 280 parts of bis(3-octoxycarbonylamino)propyl ether, $C_{24}H_{48}N_2O_5$ (molecular weight 444) corresponding with 63 percent of theory relative to bis(3-aminopropyl) ether. The purity is approximately 95 percent and the melting point is 61° C.–62° C. (from ethyl acetate).

EXAMPLE 11

Agitated in a reaction vessel are 256 parts of N,N'-bis(2,2-dimethyl-3-aminopropyl)piperazine with 400 parts of O-octyl carbamate and 130 parts of n-octanol at a reflux temperature of 190° C.–200° C. for 1 hour while the ammonia is removed by distillation. At that point, an additional 650 parts of n-octanol are allowed to flow into the reaction mixture and the reaction is continued at reflux temperature for 7 hours. Unreacted octanol and O-octylcarbonate are removed by distillation up to a sump temperature of 180° C.–200° C. at 2 millibars. By transcrystallization of the residue from acetone/water, 506 parts of N,N'-bis(octoxycarbonylaminoneopentyl)-piperazine, $C_{32}H_{64}N_4O_4$ (molecular weight 568), are obtained corresponding with 89 percent of theory relative to N,N'-bis(2,2-dimethyl-3-aminopropyl)piperaxine. The melting point is 66° C.–68° C.

EXAMPLE 12

Agitated in a reaction vessel are 170 parts of 3-aminomethyl-3,5,5-trimethyl-1-aminocyclohexane with 400 parts of O-octyl carbamate and 130 parts of n-octanol-(1) at a reflux temperature of 185° C.–200° C. for 2 hours while the ammonia is removed by means of distillation. At that point, an additional 650 parts of n-octanol-(1) are allowed to flow into the reaction mixture and the reaction is continued at reflux temperature for 8 hours. The reaction mixture is filtered, and is concentrated up to a sump temperature of approximately 200° C. at 2 millibars to 3 millibars. Obtained are 448 parts of 3-(octoxycarbonylamino)methyl-3,5,5-trimethyl-1-(octoxycarbonylamino)cyclohexane, $C_{28}H_{54}N_2O_4$ (molecular weight 482), as a partially crystallizing residue corresponding with 93 percent of theory relative to 3,5,5-trimethyl-3-aminomethyl-1-aminocyclohexane. The purity is approximately 95 percent.

EXAMPLE 13

Agitated in a reaction vessel are 102 parts of diaminoneopentane with 692 parts of O-octyl carbamate and 150 parts of n-octanol-(1) at 185° C.–195° C. for 2 hours. At that point, an additional 650 parts of n-octanol are allowed to flow into the reaction mixture and the reaction is continued at reflux temperature for 8 hours. n-Octanol and O-octyl-carbamate are removed from the reaction mixture by means of distillation up to a sump temperature of approximately 200° C. at 2 bars to 3 bars. The residue is absorbed in hot ethyl acetate, and the 5,5-dimethyl-hexahydropyrimidine-2-on, which crystallizes upon cooling, is removed by means of filtration. After removing the solvent from the filtrate by means of distillation, 178 parts of bis(octoxycarbonylamino)neopentane, $C_{23}H_{46}N_2O_4$ (molecular weight 414), are obtained as residue corresponding with 43 percent of theory relative to diaminoneopentane. The purity is approximately 95 percent.

EXAMPLE 14

Agitated in a reaction vessel are 5.8 parts of 1,6-hexamethylene diamine with 10.6 parts of O-ethyl carbamate and 9.2 parts ethanol at 175° C. for 12 hours while a pressure of 15 bars is adjusted in the reactor by means of a pressure valve so that the reaction mixture boils. The ammonia formed during the reaction is continuously removed by distillation accompanied by a throughput of 7 liters of nitrogen per liter of reaction mixture an hour. After completed reaction, the mixture is gas chromatographically analyzed according to the internal standard method. This shows that the conversion of 1,6-hexamethylene diamine is essentially quantitative and that 9.9 parts of 1,6-bis(ethoxycarbonylamino)hexane (76.2 percent of theory relative to reacted 1,6-hexamethylenediamine) have been formed. This corresponds with a volume-time yield of 32.2 grams per liter an hour.

EXAMPLES 15 to 20

The process of Example 14 was duplicated except that an additional 0.1 part of a catalyst was added to the reaction mixture The catalysts used, the reaction times, and the yields are summarized in the table.

TABLE

| Example | Catalyst | Time h. | Yield % | Volume-Time Yield g/l/h |
|---|---|---|---|---|
| 15 | Iron-(II)-acetate | 7 | 77.7 | 56.4 |
| 16 | Cobalt-(II)-acetate | 10 | 91.5 | 46.5 |
| 17 | Zinc-(II)-acetate | 7 | 71.5 | 51.9 |
| 18 | Zinc naphthenate | 7 | 70.0 | 50.8 |
| 19 | Vanadium trichloride | 5 | 64.6 | 65.6 |
| 20 | Manganese-(II)-acetate | 5 | 58.5 | 59.4 |

The embodiments of the invention in which an exclusive privilege or property is claimed are defined as follows:

1. A process for the preparation of an aliphatic, cycloaliphatic, and/or aliphatic-cycloaliphatic di- and/or polyurethane comprising the steps of
A. reacting a primary aliphatic, cycloaliphatic, and/or aliphatic-cycloaliphatic di- and/or polyamine with an O-alkyl carbamate in the presence of an alcohol at temperatures of 160° C. to 300° C., and
B. separating the ammonia and other by-products from the aliphatic and/or cycloaliphatic di- and/or polyurethane.

2. The process of claim 1 carried out in the presence of one or more catalysts wherein the catalyst is a compound containing, in bonded form, one or more cations of metals selected from the groups consisting of groups IA, IB, IIA, IIB, IIIA, IIIB, IVA, IVB, VA, VB, VIB, VIIB, and VIIIB of the periodic system.

3. The process of claim 1 or 2 wherein the reactants are present in such quanities that the ratio of amino groups of the primary aliphatic, cycloaliphatic, and/or aliphatic-cycloaliphatic di- and/or polyamine to the O-alkyl carbamate is 1:0.8 to 10.

4. The process of claim 1 or 2 wherein the reactants are present in such quantities that the ratio of amino groups of the primary aliphatic, cycloaliphatic, and/or aliphatic-cycloaliphatic di- and/or polyamine to the hydroxyl groups of the alcohols is 1:0.25 to 50.

5. The process of claim 1 or 2 wherein the ammonia by-product is continuously separated from the system as it is formed.

6. The process of claim 1 or 2 wherein the reaction is carried out at pressures of 0.1 bar to 120 bars.

7. The process of claim 1 or 2 wherein the diamine is 1,6-hexamethylenediamine.

8. The process of claim 1 or 2 wherein the diamine is selected from the group consisting of 1,4-hexahydroxylenediamine, 2,4- and 2,6- hexahydrotoluenediamine, the corresponding isomer mixtures thereof, 4,4'-diaminodicyclohexymethane, 1,4-diaminocyclohexane, 2,2-bis(4-aminocyclohexyl)propane and 3-aminomethyl-3,5,5-trimethylcyclohexylamine.

9. The process of claim 1 or 2 wherein the O-alkyl carbamates used are those of carbamic acid and aliphatic and cycloaliphatic monoalcohols having 1 to 10 carbon atoms in the alcohol radical.

10. The process of claim 1 or 2 wherein the alcohols used contain an alkyl group which corresponds to the alkyl group of the O-alkyl carbamates.

11. The process of claim 1 or 2 comprising
A. condensing the reactants in a ratio of amino groups of the amine to O-alkyl carbamate to alcohol of 1:1–1.5:0.1–1 for one hour to four hours, and
B. adding alcohol to the reaction mixture in an amount such that the ratio of amino groups of the amines to hydroxyl groups of the alcohol is 1:1.5–7.5 and such that the reaction is thereupon completed.

* * * * *